United States Patent
Hill

(10) Patent No.: US 11,918,701 B2
(45) Date of Patent: Mar. 5, 2024

(54) POLYMER COATING FOR MEDICAL DEVICES AND METHOD OF MANUFACTURE THEREOF

(71) Applicant: Mott Corporation, Farmington, CT (US)

(72) Inventor: Alex Hill, South Windsor, CT (US)

(73) Assignee: MOTT CORPORATION, Farmington, CT (US)

( * ) Notice: Subject to any disclaimer, the term of this patent is extended or adjusted under 35 U.S.C. 154(b) by 0 days.

(21) Appl. No.: 17/947,265

(22) Filed: Sep. 19, 2022

(65) Prior Publication Data

US 2023/0087962 A1      Mar. 23, 2023

Related U.S. Application Data

(60) Provisional application No. 63/246,012, filed on Sep. 20, 2021.

(51) Int. Cl.
*A61L 27/34* (2006.01)
*A61L 27/56* (2006.01)

(52) U.S. Cl.
CPC ............ *A61L 27/34* (2013.01); *A61L 27/56* (2013.01); *A61L 2400/12* (2013.01); *A61L 2420/02* (2013.01)

(58) Field of Classification Search
CPC ....... A01N 31/08; A61L 17/005; B82Y 30/00; C08J 7/16
See application file for complete search history.

(56) References Cited

U.S. PATENT DOCUMENTS

| | | | |
|---|---|---|---|
| 4,888,114 A | 12/1989 | Gaddis et al. | |
| 11,337,853 B2 | 5/2022 | Bianchi et al. | |
| 2003/0198968 A1 | 10/2003 | Matson | |
| 2006/0057180 A1* | 3/2006 | Chilkoti | C08J 7/16 424/422 |
| 2008/0181861 A1* | 7/2008 | Jiang | B82Y 30/00 523/105 |
| 2010/0145286 A1* | 6/2010 | Zhang | A61L 17/005 525/453 |
| 2020/0181426 A1 | 6/2020 | Cao et al. | |

FOREIGN PATENT DOCUMENTS

| | | | |
|---|---|---|---|
| KR | 102167085 B1 | 10/2020 | |
| WO | 2006116752 A2 | 11/2006 | |
| WO | 2011084661 A2 | 7/2011 | |
| WO | WO2019/237093 | * 12/2019 | ............ A61K 8/21 |

OTHER PUBLICATIONS

Zhang et al., Porous Gold Films—A Short Review on Recent Progress, May 2014, Materials, vol. 7(5), pp. 3834-3854 (Year: 2014).*

International Search Report for International Application No. PCT/US2022/043945; International Filing Date Sep. 19, 2022; dated Dec. 28, 2022; 2 pages.

Li et al.; "Trimethylamine N-oxide-derived zwitterionic polymers: A new class of ultralow fouling bioinspired materials"; Science Advances, vol. 5; 2019; pp. 1-10.

Written Opinion for International Application No. PCT/US2022/043945; International Filing Date Sep. 19, 2022; dated Dec. 28, 2022; 7 pages.

* cited by examiner

*Primary Examiner* — Dah-Wei D. Yuan
*Assistant Examiner* — Andrew J Bowman
(74) *Attorney, Agent, or Firm* — CANTOR COLBURN LLP

(57) ABSTRACT

Disclosed herein is a bio-resistant article comprising a porous metal substrate; a self-assembled monolayer disposed on the substrate; wherein the self-assembled monolayer comprises a coupling agent that has a first end that is reactively bonded to the porous metal substrate and a second end that is reactively bonded to a zwitterionic polymer. Disclosed herein too is a method comprising disposing upon a porous metal substrate a self-assembled monolayer; and bonding the zwitterionic polymer to the self-assembled monolayer.

13 Claims, No Drawings

POLYMER COATING FOR MEDICAL DEVICES AND METHOD OF MANUFACTURE THEREOF

CROSS-REFERENCE TO RELATED APPLICATION

The present application claims priority benefit to a provisional application which was filed on Sep. 20, 2021, and assigned Ser. No. 63/246,012. The entire contents of the foregoing provisional application is incorporated herein by reference.

BACKGROUND

This disclosure relates to a polymer coating for medical devices and methods of manufacture thereof. Biofouling occurs when microorganisms, plants, fungi, algae, or animals attach to surfaces through non-specific protein adsorption. Because biofouling can occur almost anywhere when water is present, biofouling poses a risk to many industries, including medical devices, maritime transport, pharmaceuticals, metallography, petroleum refining, and petrochemicals.

Coating a metal surface enhances biofouling resistance. Self-assembled monolayers can coat and functionalize the surface of a material. Polymeric coatings can be applied to a surface to react with the surface, or alternatively, they can be disposed on the surface to protect the surface even though there is no reaction with the surface. Some of the polymers that are used to coat surfaces include polyethers, polysaccharides such as dextran, hydrophilic polymers such as polyvinylpyrrolidone, hydroxyethyl-methacrylate, or heparin.

Despite the advances in surface coating to overcome biofouling, a need exists for improved polymers that resist biofouling and maintain their capability over prolonged exposure in solution.

SUMMARY

Disclosed herein is a bio-resistant article comprising a porous metal substrate; a self-assembled monolayer disposed on the substrate; wherein the self-assembled monolayer comprises a coupling agent that has a first end that is reactively bonded to the porous metal substrate and a second end that is reactively bonded to a zwitterionic polymer.

Disclosed herein too is a method comprising disposing upon a porous metal substrate a self-assembled monolayer; and bonding the zwitterionic polymer to the self-assembled monolayer.

DETAILED DESCRIPTION

The disclosure relates to bio-resistant porous metal surfaces that are protected from biofouling by a zwitterionic polymer coating disposed on the porous metal surface. The zwitterionic polymer coating is covalently or ionically reacted (bonded) to the metal surface via a coupling agent. In an embodiment, one portion of the coupling agent is reactively bonded to the zwitterionic polymer while another portion is reactively bonded to the porous metal surface. The zwitterionic polymer protects the surface from biofouling.

In one embodiment, a method of providing the bio-resistant coating comprises disposing a self-assembled monolayer (SAM) coating on the porous metal surface. This monolayer comprises a coupling agent with a functional group, such as a silane or thiol, that can bond to the porous metal matrix. The other end of the coupling agent comprises an initiator, such as a bromine functional group, that has the potential to polymerize a monomer to produce the zwitterionic polymer. Once coated with the SAM, the porous metal surface is immersed in a solution comprising a precursor to the polymer. After the immersion, an initiator is added to the solution to polymerize the monomer. The polymer reacts with the coupling agent to form a coating on the surface of the porous metal. The coating is one the order 10-10,000 nanograms/square centimeter ($ng/cm^2$) loading and preferably less than 1 micrometer in thickness.

As noted above the zwitterionic polymer is disposed on a porous metal surface. The porous metal surface is part of a porous metal matrix. The porous metal matrix (also sometimes referred to herein as a porous metal foam) may be used for filtration of biological fluids and hence gets subjected to biofouling over time. The porous metal matrix is porous throughout (i.e., it contains a plurality of porous percolating pathways) and permits fluids to flow through them while retaining a filtrate that has a particle size that cannot pass through the pores.

The porous metal matrix preferably comprises a plurality of open cell structures though it may include a portion of closed cell structures. The porous metal matrix may comprise a metal such as iron, zinc, magnesium, aluminum, gold, platinum, stainless steel, titanium, tantalum, iridium, molybdenum, niobium, palladium, chromium, or alloys thereof. The porous metal matrix may also comprise a layer of metal oxides disposed on a surface of the metal pores. Suitable metal oxides include oxides of the metals (that may be used in the porous metal matrix) listed above. Other metal oxides that may be used to coat the surface of the porous metal matrix include tantalum oxide, titanium oxide, iridium oxide, niobium oxide, zirconium oxide, tungsten oxide, rhodium oxide, or a combination thereof.

The diameter of the porous metal matrix used for filtration can be 0.2 millimeters to 50 millimeters, preferably 0.5 millimeters to 25 millimeters, and more preferably 0.75 millimeters to 20 millimeters. The average pore diameter of the pores is about 10 nanometers to about 10 micrometers, preferably about 100 nanometers to about 1 micrometer.

The coupling agent couples the zwitterionic polymer to the porous metal matrix surface. The coupling agent forms a reactive self-assembled monolayer on the surface of the porous metal matrix with one end reactively bonded to a surface of the porous metal matrix and an opposing end (of the coupling agent) reactively bonded to the zwitterionic polymer.

One end of the coupling agent reactively bonds to the porous metal surface and comprises a reactive functionality that can covalently or ionically bond to the metal surface under the appropriate conditions. The coupling agent comprises a first reactive functionality, a linking species that is covalently or ionically bonded to the first reactive functionality at a first end and is covalently or ionically bonded to a second reactive halogenated functionality at a second end that is opposed to the first end.

The first reactive functionality is capable of reacting with the metal or metal oxide that form the porous metal matrix. The first reactive functionality does not undergo degradation in the presence of the biological fluid that is to be filtered. It is also inert to the biological fluid and does not react with it. It does function to facilitate prevention of biofouling (especially in conjunction with the zwitterionic polymer).

Examples of the first reactive functionalities include silanes, thiols, carboxyls, amides, imides, esters, sulfate esters, phosphate esters, thiophosphate esters, borate esters, ureas, epoxides, carbamates, thiocarbamates, thiosulfates, sulfonates, phosphonates, halogen thiophosphonates, nitro, nitroso, nitrates, nitrites, or the like, or a combination thereof. Preferred reactive functionalities include silanes, thiols, or a combination thereof.

The linking species generally comprises a linear or cyclic, substituted or unsubstituted $C_2$ to $C_{30}$ alkyl, a polysiloxane polymer having 2 to 30 repeat units, or the like. In a preferred embodiment, the linking species generally comprises a linear or cyclic, substituted or unsubstituted $C_4$ to $C_{15}$ alkyl, a polysiloxane polymer having 4 to 20 repeat units, or the like. In a preferred embodiment, the linking species comprises mercaptoundecanol.

The second end of the coupling agent generally comprises a catalytic reactive functionality that facilitates polymerization of a monomer into the zwitterionic polymer. The second end of the organic complex comprises an initiator, such as a bromine functional group, that has the potential to polymerize with a monomer of the zwitterionic polymer. Examples of this initiator are shown below.

A suitable initiator is bromoisobutyryl bromide having a structure shown in formula (1) below:

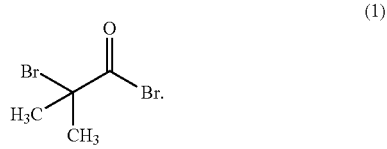

(1)

Another suitable initiator is ethyl α-bromoisobutyrate shown in formula (2)

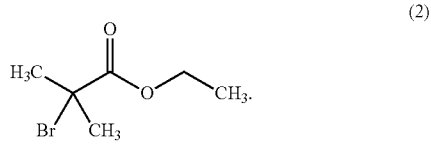

(2)

Yet another suitable initiator is 2-bromo-2-methylpropionic acid shown in formula (3)

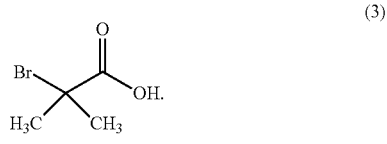

(3)

Yet another suitable initiator is 2-bromopropionyl bromide shown in formula (4)

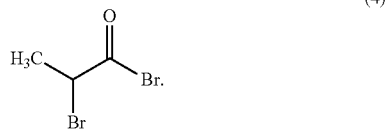

(4)

Combinations of the foregoing initiators can be used.

As noted above, a zwitterionic polymer may be initiated by the initiator. Zwitterionic polymers, including polyampholytes and polybetaines, are polymers with both positive and negative charges incorporated into their structure. Zwitterionic polymers are characterized with equal anion and cation groups on the molecular chains, which make them highly hydrophilic and antifouling. They can resist nonspecific protein adsorption, bacterial adhesion, and biofilm formation. Therefore, they have great potential to be applied in a wide range of biological and medical related fields, such as antifouling coatings of biomedical implants, blood contacted sensor and drug delivery in vivo, separation membrane and marine coatings.

Suitable polymers for the polymer coating include, but are not limited to, poly ethers, polysaccharides, polyethylene glycol, poloxamers, hydrophilic polymers, and zwitterionic polymers. Hydrophilic polymers include, but are not limited to, polyvinylpyrrolidone, hydroxyethyl-methacrylate, heparin, or a combination thereof. Although a hydrophilic polymer coating on porous metal or metal oxide materials provides some protection from biofouling with hydrophilic polymer coatings, zwitterionic polymer coatings perform well to overcome the biofouling compared with other commercially available hydrophilic polymer coatings. Zwitterionic polymers include, but are not limited to, polyphosphorylcholine (PPC), polysulfobetaine (PSB), polycarboxybetainehave (PCB), and polytrimethylamine N-oxide (PTMAO). PTMAO has been recently discovered as the fourth class to a promising zwitterionic polymer to overcome biofouling issues. PTMAO-coated surfaces exhibit low protein adsorption in blood serum and low immunogenicity. PTMAO coated surface are preferred.

In one embodiment, in one manner of manufacturing the bio-resistant porous metal, a self-assembled monolayer (SAM) coating would be first applied to the porous metal matrix. This monolayer comprises an organic complex (the coupling agent) with a functional group, such as a silane or thiol, that can bond to the porous metal matrix. The other end of the organic complex comprises the initiator, such as a bromine functional group, that has the potential to polymerize a monomer to form the polymer coating.

Once coated with the SAM, the porous matrix would be submerged within a solution containing chemical precursors to the polymer coating. Once submerged, the initiator would be added along with heat to polymerize the chemical precursors to form the coating on the surface of the porous metal. The coating would be extremely thin, on the order of 10-10,000 nanograms per square centimeter ($ng/cm^2$) loading and preferably below 1 micrometer in thickness. In an embodiment, the polymer coating has a thickness of less than 1000 nanometers, preferably less than 900 nanometers, preferably 30 to 750 nanometers.

Suitable solvents may be used during the reaction in order to permit miscibility between the precursors and the coupling agents that are bonded to the porous metal surface. Examples of polar solvents are water, propylene carbonate, ethylene carbonate, butyrolactone, acetonitrile, benzonitrile, nitromethane, nitrobenzene, sulfolane, dimethylformamide, N-methylpyrrolidone, methanol, ethanol, propanol, isopropanol, butanol, dichloromethane, or the like, or a combination thereof may be used. Other non-polar solvents such a benzene, toluene, methylene chloride, carbon tetrachloride, hexane, diethyl ether, tetrahydrofuran, or the like, or a combination thereof may also be used. Co-solvents comprising at least one polar solvent and at least one non-polar solvent may also be utilized to modify the swelling power of the solvent or to change the rate of reactivity.

The zwitterionic polymer coating on the porous metal surface is advantageous in that it overcomes the currently existing toxicity issue with polyethylene glycol coatings. It also functions better than hydrogels that sometimes do not bond or adhere well to the porous substrate.

Aside from use in medical devices, this bio-resistant coating may be used in spargers. The zwitterionic polymer may also be coated on spargers or aeration devices where bio-fouling occurs.

EXAMPLES

Example 1

This prophetic example details the preparation of the bio-resistant coating on a metal surface. In particular, this prophetic example details coating the porous metal with a self assembled monolayer of the coupling agent. 100 milliliters (ml) of dichloromethane, 1.8 ml of pyridine and 5 grams of mercaptoundecanol are first combined in a reactor at 0 to 10° C. 6.28 grams of bromoisobutyryl bromide are added to the reactor following which the contents of the reactor are mixed for one hour. The reactor is heated to 20 to 30° C. overnight (preferably for 16 hours). The solution in the reactor is then diluted with water (200 ml) and toluene (50 ml). The product is then removed from the immiscible solution via extraction of the toluene. The product, currently dissolved in the toluene, is then evaporated via reducing the pressure below its vapor pressure at room temperature. Following this, the solids are redissolved in ethanol to make a 0.2 mM solution of mercaptoundecanol and bromoisobutyryl bromide product. The porous metal substrate, specifically made from zinc in this embodiment is then soaked in the 0.2 mM solution for 24 hours. This reaction produces a porous metal with the SAM disposed thereon.

Example 2

This prophetic example discloses the formation of the zwitterionic coating on the porous metal surface. To the coated metal (from Example 1) in the solution is added copper bromide (CuBr) to get a 0.1 mM to 0.4 mM solution. This chemical when combined with Tris[2-(dimethylamino)ethyl]amine (Me$_6$TREN) forms a ligand, which acts as an initiator for the atom transfer radical polymerization (ATRP) of the PTMAO monomer. To the reactor containing the porous metal with the SAM disposed thereon add 1.72 grams of the PTMAO monomer. To the separate reactor add 2.5 to 5 ml of methanol. Add Me6TREN to get 0.05 to 0.2 mM solution. Add 0.4 ml of deionized water up to 1 mL. Mix the contents at 20 to 50° C. The reaction is continued for 8 to 24 hours till PTMAO of a desired molecular weight is formed. The reaction product which includes a coating of the PTMAO on the porous metal is then washed 2 times in methanol followed by washing 1 time in water. It is then dried in air at 20° C. to form the bio-resistant porous metal.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

Example 3

This is an actual example and was actually conducted. Using the methodology outlined in Examples 1 and 2, porous zinc samples with a maximum pore size determined via ASTM F316-03 to be roughly 3 to 3.5 microns and a mean pore size determined via capillary flow porometry to be between 0.08 to 0.12 microns were coated with PTMAO. Both a set of coated samples and a control set of uncoated samples were submerged in a solution of bovine serum albumin in de-ionized water at a concentration of 40 g/L. The control samples experienced a loss in interconnected porosity, with the protein in the solution completely fouling and plugging the samples' pores within 3 days. The coated samples retained interconnected porosity as determined via bubble point testing per ASTM F316-03 and were not plugged for up to 13 days, representing an average increase of 433% in fouling resistance.

What is claimed is:

1. A bio-resistant article comprising:
   a porous metal substrate;
   a self-assembled monolayer disposed on the substrate; wherein the self-assembled monolayer comprises a coupling agent that has a first end that is reactively bonded to the porous metal substrate and a second end that is reactively bonded to a zwitterionic polymer,
   wherein the article is a sparger.

2. The bio-resistant article of claim 1, wherein the porous metal surface comprises a metal; wherein the metal comprises iron, zinc, magnesium, aluminum, gold, platinum, stainless steel, titanium, tantalum, iridium, molybdenum, niobium, palladium, chromium, or alloys thereof.

3. The bio-resistant article of claim 1, wherein the porous metal surface has an average pore diameter of about 10 nanometers to about 100 micrometers.

4. The bio-resistant article of claim 3, wherein the porous metal surface has an average pore diameter of about 100 nanometers to about 1 micrometer.

5. The bio-resistant article of claim 1, wherein the porous metal surface comprises a metal oxide; wherein the metal oxide comprises tantalum oxide, titanium oxide, iridium oxide, niobium oxide, zirconium oxide, tungsten oxide, rhodium oxide, or a combination thereof.

6. The bio-resistant article of claim 1, wherein the first end comprises a first reactive functionality that comprises a silane, a thiol, a carboxyl, an amide, an imide, an ester, a sulfate ester, a phosphate ester, a thiophosphate ester, a borate ester, a urea, an epoxide, a carbamate, a thiocarbamate, a thiosulfate, a sulfonate, a phosphonate, a halogen thiophosphonate, a nitro, a nitroso, a nitrate, a nitrite, or a combination thereof.

7. The bio-resistant article of claim 1, wherein the zwitterionic polymer is polymerized from a monomer by a reactive initiator located at the second end of the coupling agent.

8. The bio-resistant article of claim 1, wherein the zwitterionic polymer is polyphosphorylcholine, polysulfobetaine, polycarboxybetaine, polytrimethylamine N-oxide, or a combination thereof.

9. The bio-resistant article of claim 1, wherein the zwitterionic polymer is polytrimethylamine N-oxide.

10. The bio-resistant article of claim 9, wherein the zwitterionic polymer forms a layer that is less than 1000 nanometers thick.

11. A method for fabricating an article comprising:
   disposing upon a porous metal substrate a self-assembled monolayer; and
   bonding a zwitterionic polymer to the self-assembled monolayer;
   wherein the article is a sparger.

12. The method of claim 11, further comprising reactively bonding the self-assembled monolayer to the substrate.

13. The method of claim 12, further comprising initiating polymerization of the zwitterionic polymer via a reactive initiating functionality disposed on an end of the self-assembled monolayer.

* * * * *